United States Patent
Pan et al.

(10) Patent No.: US 11,344,465 B2
(45) Date of Patent: May 31, 2022

(54) ELBOW JOINT REHABILITATION SYSTEM AND ELBOW JOINT REHABILITATION METHOD

(71) Applicant: METAL INDUSTRIES RESEARCH & DEVELOPMENT CENTRE, Kaohsiung (TW)

(72) Inventors: Bo-Wei Pan, Kaohsiung (TW); Sheng-Hong Yang, Kaohsiung (TW); Ping-Yi Hsieh, Kaohsiung (TW); Jian-Jia Zeng, Kaohsiung (TW); Tzyy-Ker Sue, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 494 days.

(21) Appl. No.: 16/395,253

(22) Filed: Apr. 26, 2019

(65) Prior Publication Data

US 2020/0337932 A1     Oct. 29, 2020

(51) Int. Cl.
*A61H 1/02*     (2006.01)
*A61B 5/25*     (2021.01)
(Continued)

(52) U.S. Cl.
CPC .............. *A61H 1/0277* (2013.01); *A61B 5/25* (2021.01); *A61B 5/316* (2021.01); *A61B 5/389* (2021.01);
(Continued)

(58) Field of Classification Search
CPC .......... A61H 1/0277; A61H 2201/5061; A61H 2201/1638; A61H 2201/165;
(Continued)

(56) References Cited

U.S. PATENT DOCUMENTS

| | | | |
|---|---|---|---|
| 2004/0106881 A1* | 6/2004 | McBean | A61B 5/389 601/5 |
| 2008/0009771 A1* | 1/2008 | Perry | A61H 1/0281 600/587 |

(Continued)

FOREIGN PATENT DOCUMENTS

| | | |
|---|---|---|
| CN | 101961527 B | 11/2013 |
| TW | I345969 B | 8/2011 |

*Primary Examiner* — Quang D Thanh
(74) *Attorney, Agent, or Firm* — CKC & Partners Co., LLC

(57) ABSTRACT

An elbow joint rehabilitation system and an elbow joint rehabilitation method are provided. The elbow joint rehabilitation system includes a support member, a motor, a torque sensing unit, a first electromyography sensor, a second electromyography sensor and a motor control device. In the elbow joint rehabilitation method, the support member is configured to support an arm of a patient. Thereafter, the torque sensing unit is configured to sense the torque applied on the support member to obtain a sensed arm torque signal. Then, the first electromyography sensor and the second electromyography sensor are configured to sense the muscle activities of biceps and triceps of the patient to obtain electromyography signals. Thereafter, the motor is controlled to drive the support member to perform rehabilitation in accordance with the sensed arm torque signal, the electromyography signals and a current support member position provided by the motor.

7 Claims, 4 Drawing Sheets

(51) Int. Cl.
*A61B 5/316* (2021.01)
*A61B 5/389* (2021.01)

(52) U.S. Cl.
CPC ............... *A61H 2001/0207* (2013.01); *A61H 2201/1207* (2013.01); *A61H 2201/165* (2013.01); *A61H 2201/1638* (2013.01); *A61H 2201/5007* (2013.01); *A61H 2201/5061* (2013.01); *A61H 2205/06* (2013.01)

(58) Field of Classification Search
CPC ........ A61H 2201/5007; A61H 2205/06; A61H 2001/0207; A61H 2201/1207; A61B 5/25; A61B 5/316; A61B 5/389; A61F 2/54; A61F 2/72
See application file for complete search history.

(56) References Cited

U.S. PATENT DOCUMENTS

| | | | | |
|---|---|---|---|---|
| 2008/0071386 A1* | 3/2008 | McBean | ............... | A61F 5/0127 |
| | | | | 623/25 |
| 2009/0209878 A1* | 8/2009 | Sanger | .................. | A61B 5/486 |
| | | | | 600/546 |
| 2016/0287422 A1* | 10/2016 | Kelly | ....................... | A61H 1/02 |

* cited by examiner

ELBOW JOINT REHABILITATION SYSTEM AND ELBOW JOINT REHABILITATION METHOD

BACKGROUND

Field of Invention

The present invention relates to an elbow joint rehabilitation system and an elbow joint rehabilitation method. More particularly, the present invention relates to an elbow joint rehabilitation system and an elbow joint rehabilitation method for spasm relieving.

Description of Related Art

With the development of medical technologies and the improvement of environmental health, the average life expectancy in the world has been prolonged in recent decades. However, the number of patients suffering brain and nervous diseases also increases with changes of eating habits and increase of living stress. If the central nervous system is damaged, a sequela such as limb hemiplegia would be induced, and thus the body cannot freely move. Consequently, health cares to the limb hemiplegia caused by brain or nerve damage and medical issues need to be concerned. On the other hand, more and more traffic and sports injuries happen as traffic and sports activities become more frequent. If a nerve or a muscle is damaged, the damaged part of the patient would not move normally. For a patient who has a body movement problem, the quality of rehabilitation treatment would affect the recovery effect and speed. In general, if a patient's health status can be accurately evaluated and a suitable treatment can be provided, the patient recovery status can be improved, and the rehabilitation duration of the patient can be effectively reduced.

SUMMARY

An aspect of the present invention provides an elbow joint rehabilitation system and an elbow joint rehabilitation method adapted for elbow joint rehabilitation of a patient. When spasms occur during the elbow joint rehabilitation performed, a relieving operation is performed on the arm having the spasms to protect the arm of the patient from being damaged.

The above elbow joint rehabilitation system includes a support member, a motor, a torque sensing unit, a first electromyography sensor, a second electromyography sensor and a motor control device. The support member is configured to support an arm of a patient. The motor is configured to drive the support member to perform elbow joint rehabilitation, and to provide a current position of the support member. The torque sensing unit is configured to sense the torque applied on the support member to output a sensed arm torque signal. The first electromyography sensor is configured to sense a muscle activity of biceps of the patient to output a first electromyography signal. The second electromyography sensor is configured to sense a muscle activity of triceps of the patient to output a second electromyography signal. The motor control device is electrically connected to the torque sensing unit, the first electromyography sensor, the second electromyography sensor and the motor to control the motor in accordance with the current position of the support member, the sensed arm torque signal, the first electromyography signal and the second electromyography signal.

In some embodiments, the motor control device includes an impedance control module and an impedance module. The impedance control module is configured to output an impedance adjustment signal in accordance with the current position of the support member, the first electromyography signal and the second electromyography signal. The impedance module is configured to receive the impedance adjustment signal and to provide a first torque signal in accordance with the impedance adjustment signal to adjust the torque provided by the motor.

In some embodiments, the impedance control module is further configured to determine if the motor control device performs a spasm relieving mode in accordance with the first electromyography signal and the second electromyography signal.

In some embodiments, the motor control device further includes a proportional-integral controller configured to output a second torque signal in accordance with the first torque signal to adjust the torque provided by the motor.

In some embodiments, the first electromyography sensor and the second electromyography sensor are electrodes.

In the above elbow joint rehabilitation method, at first, a support member is provided to support an arm of a patient. Then, a current position of the support member is provided by using a motor. Thereafter, the torque applied on the support member is sensed by using a torque sensing unit to obtain a sensed arm torque signal. Thereafter, a muscle activity of biceps of the patient is sensed by using a first electromyography sensor to obtain a first electromyography signal. Then, a muscle activity of triceps of the patient is sensed by using a second electromyography sensor to obtain a second electromyography signal. Thereafter, the motor is controlled in accordance with the current position of the support member, the sensed arm torque signal, the first electromyography signal and the second electromyography signal to drive the support member to perform elbow joint rehabilitation.

In some embodiments, the step for controlling the motor in accordance with the current position of the support member, the sensed arm torque signal, the first electromyography signal and the second electromyography signal includes determining if the first electromyography signal is greater than a first electromyography signal threshold to provide a first determination result; determining if the second electromyography signal is greater than a second electromyography signal threshold to provide a second determination result; and when one of the first determination result and the second determination result is no, a normal rehabilitation mode is performed.

In some embodiments, when both the first determination result and the second determination result are yes, a spasm relieving mode is performed.

In some embodiments, the normal rehabilitation mode includes: controlling the motor to drive the support member to exercise the arm of the patient within a range of bending angle, in which the range of bending angle is from 5 degrees to 90 degrees.

In some embodiments, the spasm relieving mode includes: controlling the motor to drive the support member to exercise the arm of the patient within a range of bending angle, in which the range of bending angle is from 90 degrees to 75 degrees.

BRIEF DESCRIPTION OF THE DRAWINGS

The invention can be more fully understood by reading the following detailed description of the embodiment, with reference made to the accompanying drawings as follows.

DETAILED DESCRIPTION

The using of "first", "second", "third", etc. in the specification should be understood for identifying units or data described by the same terminology but are not referred to particular order or sequence.

Figure 1:
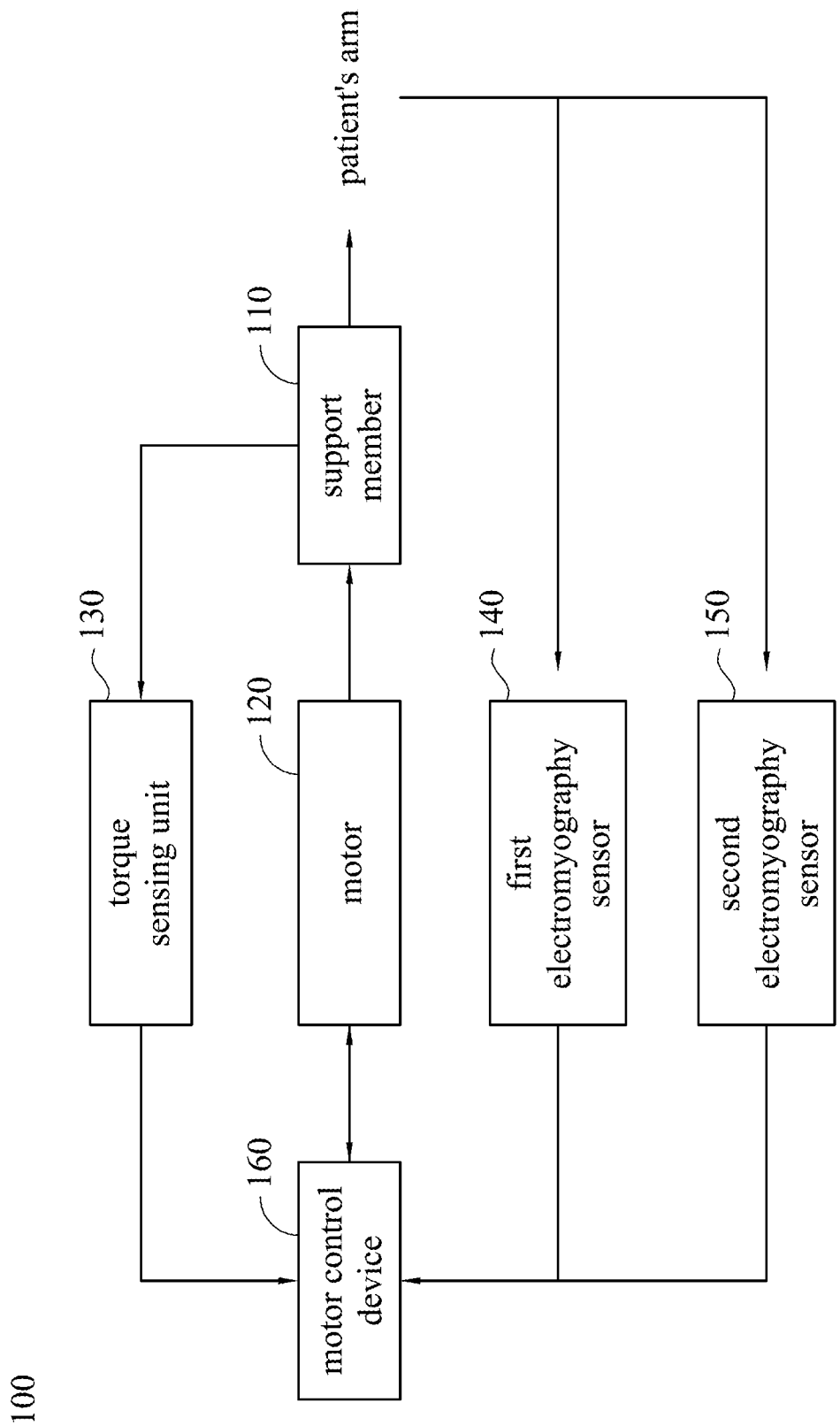
FIG. 1 is a functional block diagram of an elbow joint rehabilitation system in accordance with an embodiment of the present invention.
Figure 2:
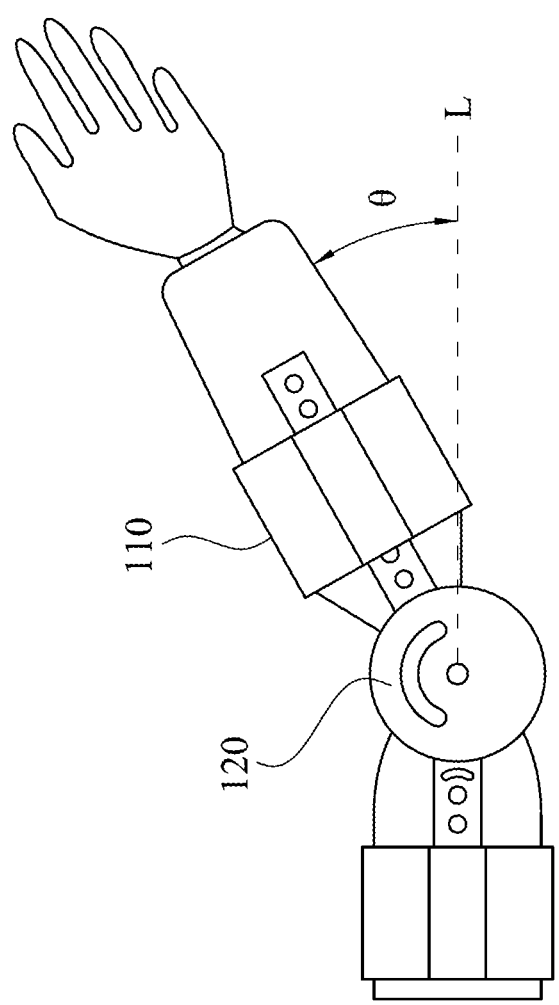
FIG. 2 is a schematic diagram showing a structure of an exoskeleton of the elbow joint rehabilitation system in accordance with an embodiment of the present invention.

Referring to FIG. 1 and FIG. 2, FIG. 1 is a functional block diagram of an elbow joint rehabilitation system 100 in accordance with an embodiment of the present invention, and FIG. 2 is a schematic diagram showing a structure of an exoskeleton of the elbow joint rehabilitation system 100 in accordance with an embodiment of the present invention. The elbow joint rehabilitation system 100 includes a support member 110, a motor 120, a torque sensing unit 130, a first electromyography sensor 140, a second electromyography sensor 150 and a motor control device 160. In an embodiment of the present invention, the exoskeleton of the elbow joint rehabilitation system 100 includes the support member 110 and the motor 120 as shown in FIG. 2, in which the support member 110 is configured to support an arm of a patient, the motor 120 is configured to drive the support member 110 to perform elbow joint rehabilitation. The motor 120 has a position sensing device (not shown) capable of providing a current position of the support member 110 that is an angle θ between the arm of the patient and a horizontal line L, in which the horizontal line L corresponds to an elbow of the patient.

The torque sensing unit 130 is configured to sense the torque applied on the support member 110 to output a sensed arm torque signal. The first electromyography sensor 140 is configured to sense a muscle activity of biceps of the patient to output a first electromyography signal. The second electromyography sensor 150 is configured to sense a muscle activity of triceps of the patient to output a second electromyography signal. In an embodiment of the present invention, the first electromyography sensor 140 and the second electromyography sensor 150 are electrodes, but embodiments of the present invention are not limited thereto. The motor control device 160 is electrically connected to the torque sensing unit 130, the first electromyography sensor 140, the second electromyography sensor 150 and the motor 120 to control the motor 120 in accordance with the current position θ of the support member 110, the sensed arm torque signal, the first electromyography signal and the second electromyography signal. In an embodiment of the present invention, the motor control device 160 is a microcontroller unit (MCU), but embodiments of the present invention are not limited thereto.

Figure 3:
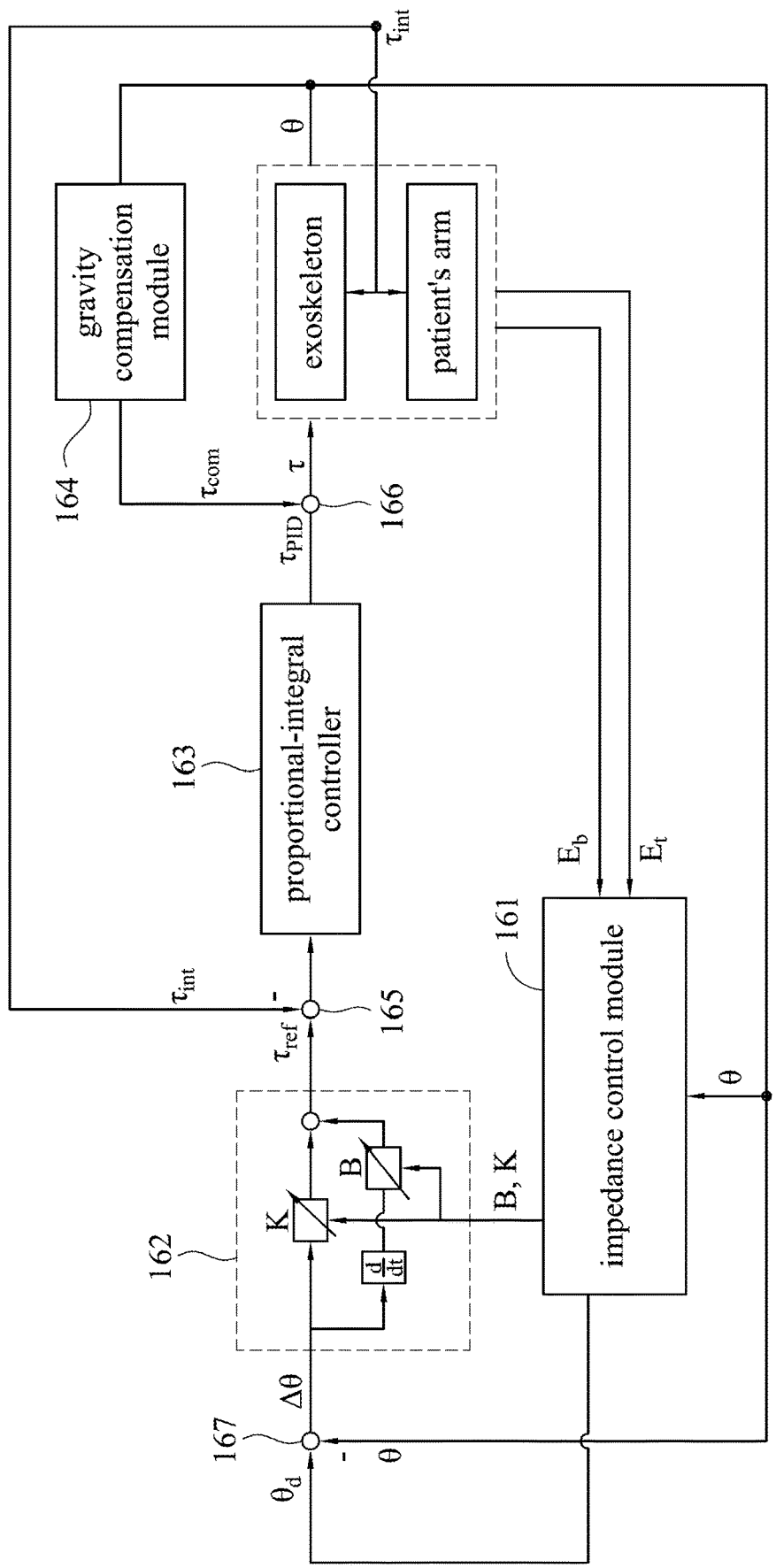
FIG. 3 is a feedback control functional block diagram of the motor control device in accordance with an embodiment of the present invention.

Referring to FIG. 3, FIG. 3 is a feedback control functional block diagram of the motor control device 160 in accordance with an embodiment of the present invention. The motor control device 160 includes an impedance control module 161, an impedance module 162, a proportional-integral controller 163 and a gravity compensation module 164. The impedance control module 161 is configured to receive the sensed arm torque signal $\tau_{int}$, the first electromyography signal $E_b$, the second electromyography signal $E_t$, and the current position θ of the support member 110, and to control the impedance module 162 in accordance with the sensed arm torque signal $\tau_{int}$, the first electromyography signal $E_b$, the second electromyography signal $E_t$, and the current position θ of the support member 110.

The impedance module 162 is configured to provide a torque signal $\tau_{ref}$ to control the resistance provided by the elbow joint rehabilitation system 100. For example, the impedance module 162 provides torque signals $\tau_{ref}$ having different values to enable the exoskeleton to provide resistance exercises having different resistances, in which the value of the torque signal $\tau_{ref}$ provided by the impedance module 162 increases with the increase of a value of a damping coefficient gain B and a value of an elasticity coefficient gain K of the impedance module 162, and the resistance provided by the elbow joint rehabilitation system 100 increases accordingly. In contrast, the value of the torque signal $\tau_{ref}$ provided by the impedance module 162 decreases with the decrease of the value of a damping coefficient gain B and the value of an elasticity coefficient gain K of the impedance module 162, and the resistance provided by the elbow joint rehabilitation system 100 decreases accordingly.

The proportional-integral controller 163 is electrically connected to the impedance module 162 and the motor 120 in the exoskeleton to control the toque provided by the motor 120 in accordance with the torque signal $\tau_{ref}$ provided by the impedance module 162. In an embodiment of the present invention, the torque sensing unit 130 provides the sensed arm torque signal $\tau_{int}$ to an adder 165, and the adder 165 outputs a difference value between the torque signal $\tau_{ref}$ and the sensed arm torque signal $\tau_{int}$ to the proportional-integral controller 163, thereby implementing negative feedback control of the sensed arm torque signal $\tau_{int}$.

The gravity compensation module 164 is configured to perform gravity compensation on the torque signal $\tau_{PID}$ outputted by proportional-integral controller 163 to reduce the influence caused by gravity. For example, the gravity compensation module 164 outputs a torque signal $\tau_{COM}$ in accordance with the current position θ of the support member 110, and an adder 166 calculates a torque difference τ between the torque signal $\tau_{PID}$ and the torque signal $\tau_{COM}$, and then the torque difference τ is outputted to the motor 120 in the exoskeleton to enable the motor 120 to drive the support member 110 in accordance with the torque difference τ.

In the embodiments of the present invention, the elbow joint rehabilitation includes a normal rehabilitation mode and a spasm relieving mode. The normal rehabilitation mode is used to rehabilitate the arm of the patient, and the spasm relieving mode is used to relax the muscle of the arm of the patient when spasms occur in the arm, thereby relieving the spasms in the arm of the patient. The impedance control module 161 determines if the spasms occur in the arm of the patient in accordance with first electromyography signal $E_b$ and the second electromyography signal $E_t$ to provide the normal rehabilitation mode or the spasm relieving mode accordingly.

After the first electromyography signal $E_b$ and the second electromyography signal $E_t$ are received by the impedance control module 161, the impedance control module 161 determines if the spasms occur in the arm of the patient in accordance with first electromyography signal $E_b$ and the second electromyography signal $E_t$. For example, the impedance control module 161 determines if the first electromyography signal $E_b$ is greater than a first electromyography signal threshold and determines if the second electromyography signal $E_t$ is greater than a second electromyography signal threshold. If the first electromyography signal $E_b$ is not greater than the first electromyography signal threshold, or the second electromyography signal $E_t$ is not greater than a second electromyography signal threshold, the impedance control module 161 determines that no spasm occurs in the arm of the patient. In this case, the impedance control module 161 controls the impedance module 162 to provide the torque signal $\tau_{ref}$ corresponding to the normal rehabilitation mode. However, if the first electromyography signal $E_b$ is greater than the first electromyography signal threshold, and the second electromyography signal $E_t$ is greater than a second electromyography signal threshold, the impedance control module 161 determines that spasms occur in the arm of the patient. In this case, the impedance control module 161 controls the impedance module 162 to provide the torque signal $\tau_{ref}$ corresponding to the spasm relieving mode.

The impedance control module 161 stores plural target positions $\theta_d$ of the support member 110. In an embodiment of the present invention, the target positions $\theta_d$ of the support member 110 are arranged in plural matrixes. For example, the impedance control module 161 stores plural target position matrixes corresponding to the normal rehabilitation mode and the spasm relieving mode. In another embodiment of the present invention, the target position matrixes corresponding to the normal rehabilitation mode can be separated into a target position matrix corresponding to an active exercise and a target position matrix corresponding to a passive exercise.

In the normal rehabilitation mode, the impedance control module 161 outputs the target positions $\theta_d$ corresponding to the normal rehabilitation mode to an adder 167 in a time sequence. The adder 167 calculates a position difference $\Delta\theta$ between the target position $\theta_d$ and the current position $\theta$ of the support member 110, and provides the position difference $\Delta\theta$ to the impedance module 162. In addition, the impedance control module 161 also sets the value of the damping coefficient gain B and the value of the elasticity coefficient gain K in accordance with the current position $\theta$ of the support member 110. Therefore, the impedance control module 161 is capable of providing the torque signal $\tau_{ref}$ corresponding to the normal rehabilitation mode. In an embodiment of the present invention, the target position $\theta_d$ corresponding to the normal rehabilitation mode is ranged from 5 degrees to 90 degrees. In other words, the exercise target stored in the motor control device 160 is that the arm of the patient is gradually moved from the position of 5 degrees to the position of 90 degrees. However, the embodiments of the present invention are limited thereto.

During the period at which the normal rehabilitation mode is performed, the impedance control module 161 switches to the spasm relieving mode immediately when the impedance control module 161 determines the spasms occur in the arm of the patient. In the spasm relieving mode, the impedance control module 161 outputs the target positions $\theta_d$ corresponding to the spasm relieving mode to the adder 167 in a time sequence. The adder 167 calculates a position difference $\Delta\theta$ between the target position $\theta_d$ and the current position $\theta$, and provides the position difference $\Delta\theta$ to the impedance module 162. In addition, the impedance control module 161 also sets the values of the damping coefficient gain B and the elasticity coefficient gain K to enable the values of the damping coefficient gain B and the elasticity coefficient gain K corresponding to the spasm relieving mode are greater than the values of the damping coefficient gain B and the elasticity coefficient gain K corresponding to the normal rehabilitation mode. Therefore, the impedance control module 161 is capable of providing the torque signal $\tau_{ref}$ corresponding to the spasm relieving mode. In an embodiment of the present invention, the target position $\theta_d$ corresponding to the spasm relieving mode is ranged from 90 degrees to 75 degrees. In other words, the exercise target stored in the motor control device 160 is that the arm of the patient is gradually moved from the position of 90 degrees to the position of 70 degrees. However, the embodiments of the present invention are limited thereto.

In addition, it is noted that a doctor may manually control the impedance control module 161 to switch to the spasm relieving mode when the doctor is aware that the spasms occur in the arm of the patient, thereby relieving the spasms in the arm of the patient.

Figure 4:
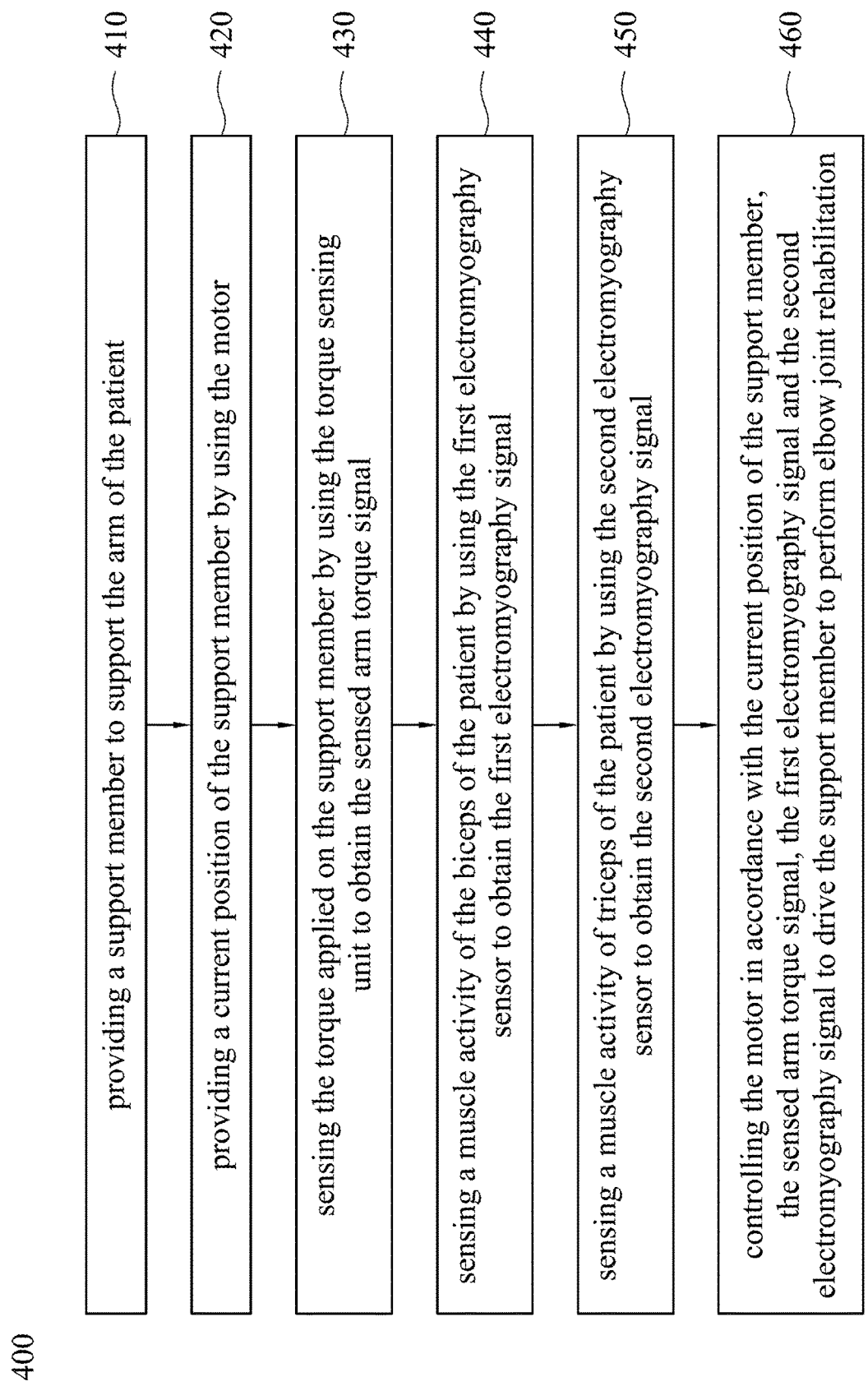
FIG. 4 is a flow chart showing an elbow joint rehabilitation method in accordance with an embodiment of the present invention.

Referring to FIG. 4, FIG. 4 is a flow chart showing an elbow joint rehabilitation method 400 in accordance with an embodiment of the present invention. In the elbow joint rehabilitation method 400, at first, step 410 is performed to use the support member 110 to support the arm of the patient. Thereafter, step 420-450 are performed to use the motor 120, the torque sensing unit 130, the first electromyography sensor 140, the second electromyography sensor 150 and the motor control device 160 to obtain the current position of the support member 110, the sensed arm torque signal, the first electromyography signal and the second electromyography signal. Then, step 460 is performed to control the motor 120 in accordance with the current position of the support member 110, the sensed arm torque signal, the first electromyography signal and the second electromyography signal to enable the motor 120 to drive the support member 110 for the elbow joint rehabilitation. In step 460, it is determined that if spasms occur in the arm of the patient in accordance with the first electromyography signal and the second electromyography signal. If the spasms occur in the arm of the patient, the spasm relieving mode is performed to relieve the spasms in the arm of the patient. If no spasm occurs in the arm of the patient, the normal rehabilitation mode is performed to rehabilitate the arm of the patient.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:
1. An elbow joint rehabilitation system comprising:
a support member configured to support an arm of a patient;
a motor configured to drive the support member to perform elbow joint rehabilitation, and to provide a current position of the support member;
a torque sensing circuit configured to sense a torque applied on the support member to output a sensed arm torque signal;

a first electromyography sensor configured to sense a muscle activity of biceps of the patient to obtain a first electromyography signal;

a second electromyography sensor configured to sense a muscle activity of triceps of the patient to obtain a second electromyography signal; and a motor control device electrically connected to the torque sensing circuit, the first electromyography sensor, the second electromyography sensor and the motor to control the motor in accordance with the current position of the support member, the sensed arm torque signal, the first electromyography signal and the second electromyography signal.

2. The elbow joint rehabilitation system of claim 1, wherein the motor control device comprises:

an impedance control circuit configured to output an impedance adjustment signal in accordance with the current position of the support member, the first electromyography signal and the second electromyography signal; and an impedance circuit configured to receive the impedance adjustment signal and to provide a first torque signal in accordance with the impedance adjustment signal to adjust a torque provided by the motor.

3. The elbow joint rehabilitation system of claim 2, wherein the impedance control circuit is further configured to determine whether the motor control device performs a spasm relieving mode in accordance with the first electromyography signal and the second electromyography signal.

4. The elbow joint rehabilitation system of claim 2, wherein the motor control device further comprises a proportional-integral controller configured to output a second torque signal in accordance with the first torque signal to adjust the torque provided by the motor.

5. The elbow joint rehabilitation system of claim 1, wherein the first electromyography sensor and the second electromyography sensor are electrodes.

6. An elbow joint rehabilitation method comprising:

providing a support member to support an arm of a patient;

providing a current position of the support member by using a motor;

sensing a torque applied on the support member by using a torque sensing circuit to obtain a sensed arm torque signal;

sensing a muscle activity of biceps of the patient by using a first electromyography sensor to obtain a first electromyography signal;

sensing a muscle activity of triceps of the patient by using a second electromyography sensor to obtain a second electromyography signal; and controlling the motor in accordance with the current position of the support member, the sensed arm torque signal, the first electromyography signal and the second electromyography signal to enable the motor to output torque corresponding to a gravity direction to drive the support member to perform elbow joint rehabilitation;

wherein the controlling the motor in accordance with the current position of the support member, the sensed arm torque signal, the first electromyography signal and the second electromyography signal comprises:

determining whether the first electromyography signal is greater than a first electromyography signal threshold to provide a first determination result;

determining whether the second electromyography signal is greater than a second electromyography signal threshold to provide a second determination result;

when one of the first determination result and the second determination result is no, a normal rehabilitation mode is performed; and when both the first determination result and the second determination result are yes, a spasm relieving mode is performed;

wherein the spasm relieving mode comprises:

outputting a plurality of target positions of the support member corresponding to the spasm relieving mode in accordance with a predetermined time sequence;

calculating a position difference between each of the target positions of the support member and a current position of the support member; and adjusting a torque provided by the motor in accordance with the position difference accordingly to control the movement of the support member in accordance with the target positions of the support member, thereby achieving spasm relieving for the patient.

7. The elbow joint rehabilitation method of claim 6, wherein the normal rehabilitation mode comprises:

controlling the motor to drive the support member to exercise the arm of the patient within a range of bending angle of the arm of the patient, wherein the range of bending angle is from 5 degrees to 90 degrees.

* * * * *